United States Patent [19]

Terayama

[11] 4,263,897
[45] Apr. 28, 1981

[54] ENDOSCOPE

[75] Inventor: Toshiki Terayama, Kodaira, Japan

[73] Assignee: Olympus Optical Co., Ltd., Tokyo, Japan

[21] Appl. No.: 35,807

[22] Filed: May 4, 1979

[51] Int. Cl.³ .......................... A61B 1/12; A61B 1/30
[52] U.S. Cl. ...................................................... 128/7
[58] Field of Search ....................................... 128/3–8, 128/240, 241; 138/134, 131, 139

[56] References Cited

U.S. PATENT DOCUMENTS

| 434,748 | 8/1890 | Almond | 138/134 |
|---|---|---|---|
| 2,176,391 | 10/1939 | Chalmers | 128/241 X |
| 2,558,763 | 7/1951 | Lee | 138/139 X |
| 3,771,522 | 11/1973 | Waysilk et al. | 128/240 X |

FOREIGN PATENT DOCUMENTS

| 1791280 | 7/1974 | Fed. Rep. of Germany | 128/4 |
|---|---|---|---|
| 400531 | 7/1909 | France | 128/241 |

Primary Examiner—Robert W. Michell
Assistant Examiner—Arthur S. Rose

[57] ABSTRACT

An endoscope consists of a sheath having a passage extending therethrough, a water-feeding inlet portion and a water-draining outlet portion disposed near the proximal end portion of the sheath and each having a valve. The inlet portion and the outlet portion are provided with connection hoses each consisting of two layers of flexible coil tubes. The flexibility of the connection hose can set the inlet and outlet portions in any direction, thereby enabling the endoscope to be easily handled without being obstructed by the inlet and outlet portions.

4 Claims, 4 Drawing Figures

ENDOSCOPE

BACKGROUND OF THE INVENTION

This invention relates to an endoscope such as a fiberscope for a urinary bladder or for a uterus which is provided with water-feeding inlet and water-draining outlet for affusion of a body cavity such as a urinary bladder or womb.

FIG. 1 illustrates the prior art endoscope for a urinary bladder or uterus, which comprises an outer tube 1 and a body cavity observing telescope tube 2 inserted thereinto. The proximal end of the outer tuber 1 is fitted with a grip 4, water-feeding inlet portion 5 and water-draining outlet portion 6. These portions 5, 6 are respectively connected to a water-feeding tube 7 and water-draining tube 8. Water is conducted through the outer tube 1 into and out of a body cavity at the distal end of the endoscope, thereby effecting the affusion of the interior of the body cavity.

Where a womb or a urinary bladder is examined by an endoscope, it is necessary to change the position of the endoscope or the direction in which the endoscope is set by turning the endoscope about its axis in a patient's womb or taking the endoscope into or out of the womb or urinary bladder.

With the prior art endoscope of FIG. 1, however, the water-feeding inlet portion 5 and water-draining outlet portion 6 are made of a rigid metal tube, and are extended at right angles to the axis of the endoscope. The water-feeding and water-draining tubes 7, 8 which are respectively fitted into the portions 5, 6 are extended at right angles to the axis of the endoscope. Consequently, the water-feeding and water-draining tubes 7, 8 sometimes strike against a patient's opened feet, or touch an operator's hands or face, or are fastened about the operator's hands, thereby tending to obstruct an medical examination.

SUMMARY OF THE INVENTION

It is accordingly the object of this invention to provide an endoscope in which water-feeding inlet portion and water-draining outlet portion are made to be freely bent in any direction with respect to the corresponding fitting members, thereby preventing water-feeding and water-draining tubes from obstructing a medical examination.

According to the invention, there is provided an endoscope comprising a sheath which is adapted for insertion into a body cavity, and provided with water-feeding and water-draining passages communicating with the body cavity at the distal end of the endoscope and water-feeding inlet portion and water-draining outlet portion which are bendably fitted to the proximal end of the outer tube to communicate with the water-feeding and water-draining passages.

BRIEF DESCRIPTION OF THE DRAWING

This invention can be fully understood from the following description with reference to the accompanying drawings in which.

DESCRIPTION OF THE PREFERRED EMBODIMENT

Figure 1:
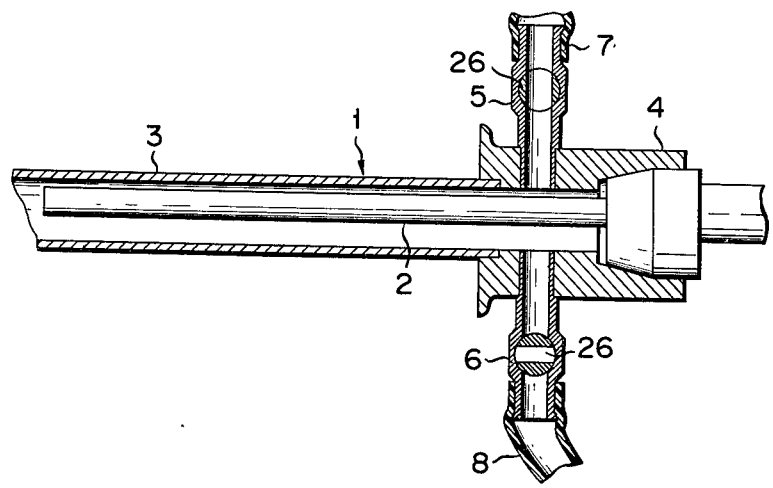
FIG. 1 is a longitudinal sectional view of the main section of a known endoscope provided with water-feeding and water-draining passages.
Figure 2:
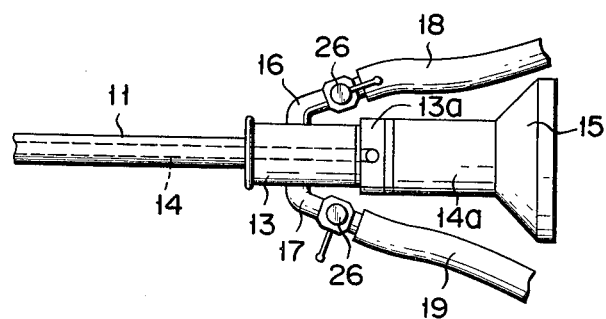
FIG. 2 is a plan view of the main section of an endoscope embodying this invention.

There will now be described by reference to FIGS. 2 to 4 an endoscope embodying this invention used, for example, as a womb fiberscope or urinary bladder fiberscope adapted for affusion of an internal organ or body cavity such as womb or urinary bladder.

The endoscope comprises a rigid hollow cylindrical sheath 11 and a grip member 13 fixed to the proximal end of the sheath 11. A common passage 12 (FIG. 3) is extended through the sheath 11 and grip member 13. The passage 12 opens at the distal end of the sheath 11. An optical system-receiving tube 14 (FIG. 2) is detachably inserted into the common passage 12. The proximal end of the optical system-receiving tube 14 is provided with a larger diameter section 14a. That end of this larger diameter section 14a which is nearer to the optical system-receiving tube 14 is engaged in a liquid-tight stage with a flange 13a formed at the proximal end of the grip member 13 to seal the common passage 12. The proximal end of the larger diameter section 14a is provided with an eyepiece 15. The optical system-receiving tube 14 contains an illumination optical system for illuminating the interior of the body cavity at the distal end (not shown) of the endoscope, and an observation optical system for receiving an image showing the interior condition of the body cavity. These illumination and observation optical systems used with the endoscope of this invention which are of the known type are not indicated in the accompanying drawing. Nor are shown an illumination power source and a cord for connecting the power source to the illumination optical system.

A flexible water-feeding inlet portion 16 and flexible water-draining outlet portion 17 are projectively provided in a diametically opposite relationship on the peripheral surface of the grip member 13 of the sheath 11. The free ends of the water-feeding inlet portion 16 and water-draining outlet portion 17 are respectively connected to the corresponding ends of a water-feeding tube 18 and water-draining tube 19. The opposite ends of these water-feeding and water-draining tubes 18, 19 are connected to the known water supply device and water suction device.

Figure 3:
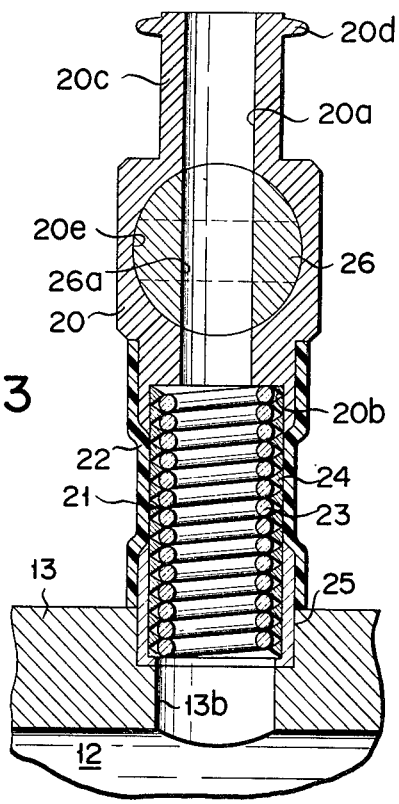
FIG. 3 is a longitudinal sectional view of the water-feeding inlet portion and water-draining outlet portion.
Figure 4:
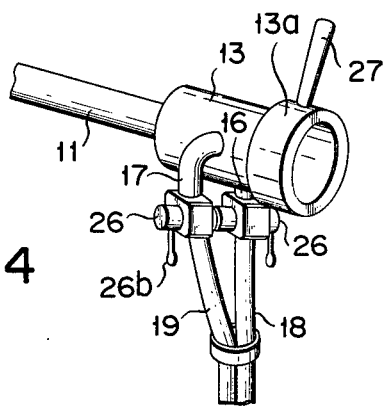
FIG. 4 is a perspective view of the main section of the endoscope embodying the invention.

As shown in FIG. 3, the water-feeding inlet portion 16 and water-draining outlet portion 17 have the same construction. An annular fitting member 25 made of non-corrosive material such as stainless steel is fixedly inserted into a communication passage 13b defined by the inner lateral wall of the grip member 13 in a concentrical relationship with said passage 13b. A connection hose 21 is formed of a first coil tube 23 constructed by helically winding a flexible stainless steel wire having a circular cross section and a second coil tube 24 constructed by helically winding the same stainless steel wire having a triangular cross section around the first coil tube 23 at the same pitch as the turns of the first coil tube 23, with one of the apical portions of the triangular cross section of the wire constituting the second coil tube 24 directed inward. One end of the second coil tube 24 is securely inserted into the annular fitting member 25. In this case, the apical point of the triangular cross section of the wire of the second coil tube 24 is inserted between the adjacent turns of the first coil tube 23. Both said planes of the apical point of the triangular cross section of the second coil tube wire are pressed against the peripheral surfaces of the corresponding turns of the first coil tube 23. The connection hose 21 formed of the coil tubes can be bent not only in any desired direction but also sustain said bent state by the wedge action between the circular cross section of the wire constituting the first coil tube 23 and the triangular cross section of the wire constituting the second coil tube 24.

Provided in substantially cylindrical valve member 20 is a concentric cylindrical passage 20a. This passage 20a is provided at one end with a larger diameter section 20b, into which the other end of the hose 21 is securely inserted. The valve member 20 is provided at the other end with a smaller diameter section 20C. The free end of the valve member 20 is provided with a lip or annular projection 20d. The smaller diameter section 20c of the valve member 20 is inserted into said one end of the water-feeding tube 18 or water-draining tube 19 to seal the lip 20d in a liquid-tight state.

The valve member 20 is further provided with a cock passage 20e whose axis intersects that of the cylindrical passage 20a at right angles. Fitted into the cock passage 20e is a cylindrical cock 26 which is provided with a cylindrical passage 26a extended at right angles to the axis of the passage 20a for alignment with the passage 20e.

Where the cock 26 is rotated about its axis by operating a handle 26b fixed to the peripheral wall of that end portion of the cock 26 which protrudes from the valve member 20 to establish communication between the passages 26a and 20a as indicated in solid lines in FIG. 3, fresh wash water is supplied to the common passage 12 from a water source through the water-feeding tube 18 for affusion of the body cavity, or where required, wash water used for said affusion is drawn off from the passage 12 to a suction device through the water-draining tube 19. Further, by turning the handle 26b, it is possible, as shown in chain lines in FIG. 3, to close the passage 20a by the lateral walls of the cock 26, thereby stopping the supply or drain of water through the valve 20. During water supply, the cock 26 of the valve 20 of the water-feeding inlet portion 16 is opened, while the cock 26 of the valve 20 of the water-draining outlet portion 17 is closed. Obviously during water drain, the cock 26 of the valve 20 of the water-feeding inlet portion 16 is closed, while the cock 26 of the valve 20 of the water-draining outlet portion 17 is opened. Supply of affusion water to the body cavity and drain of the water therefrom are effected at the distal end of the endoscope.

A tough flexible sealing tube 22 prepared from, for example, polytetrafluoroethylene resin is tightly fitted around said one end of the valve 20 and that section of the annular fitting member 25 which protrudes from the lateral wall of the grip member 13, thereby sealing the connection hose 21 in a liquid-tight state.

There will now be described the operation of an endoscope embodying the invention adapted for examination or affusion of the body cavity. As previously mentioned, the connection hoses 21 of the water-feeding inlet portion 16 and water-draining outlet portion 17 can be freely bent in any direction and to any extent to facilitate the application of the endoscope. Therefore, it is possible, as illustrated in FIG. 2, to bend the water-feeding tube 18 and water-draining tube 19, with their lateral sides drawn near the endoscope body, and in this state extend the free ends of said tubes 18, 19 beyond the proximal end of the endoscope, namely, toward the eyepiece 15. Or, as seen from FIG. 4, the water-feeding tube 18 and water-draining tube 19 can be bent at right angles to the outer tube 11 to be bundled together. The above-mentioned operations can prevent the tubes 18, 19 from touching a patient's body or operator's face or hands or from being fastened about the operator's hands. Accordingly, the body cavity can be easily examined or undergo affusion by the endoscope of this invention. The water-feeding tube 18 and water-draining tube 19 can occupy any other position than indicated in FIGS. 2 and 4 most suitable for the examination or affusion of a body cavity by properly bending the connection hose 21. The connection hose 21 which can be freely bent in any direction and to any extent prevents the water-feeding tube 18 and water-draining tube 19 from being broken by forced bending, thereby eliminating the resultant stop of water flow.

What is claimed is:

1. In an endoscope for use in either one of a womb and a urinary bladder, comprising a sheath having a distal end and a proximal end for insertion into a body cavity at the distal end, a passage extending through the sheath and opened at the distal end of the sheath, a water-feeding inlet portion and a water-draining outlet portion each provided at the proximal end of the sheath, valves each provided in the inlet portion and the outlet portion, the improvement wherein at least part of the inlet portion and the outlet portion is formed into a flexible connection hose bendable in any direction and to any extent, said flexible hose including means for maintaining the position into which said flexible hose is bent.

2. The endoscope according to claim 1, wherein said connection hose comprises a coil tube formed by winding a flexible wire having a circular cross section.

3. The endoscope according to claim 2, wherein said connection hose further comprises a second coil tube formed by winding a flexible wire having a triangular cross section, said second coil tube surrounding the first-mentioned coil tube at a same pitch thereof with one of apices of the triangular section disposed between adjacent turns of the first-mentioned coil tube and with both lateral sides of the second tube adjacent to said one of the apices pressed against peripheral surfaces of the corresponding turns of the first-mentioned coil tube.

4. The endoscope according to any one of the preceding claims, wherein the connection hose is sealingly surrounded by a flexible sealing tube.

* * * * *